(12) United States Patent
Hoots et al.

(10) Patent No.: US 7,811,517 B2
(45) Date of Patent: Oct. 12, 2010

(54) METHOD OF TRACING CORROSIVE MATERIALS

(75) Inventors: John E. Hoots, Batavia, IL (US); Barbara H. Davis, Geneva, IL (US)

(73) Assignee: Nalco Company, Naperville, IL (US)

(*) Notice: Subject to any disclaimer, the term of this patent is extended or adjusted under 35 U.S.C. 154(b) by 0 days.

(21) Appl. No.: 12/042,058

(22) Filed: Mar. 4, 2008

(65) Prior Publication Data

US 2008/0160626 A1    Jul. 3, 2008

Related U.S. Application Data

(63) Continuation-in-part of application No. 10/631,607, filed on Jul. 31, 2003, now abandoned.

(51) Int. Cl.
  *G01N 23/00* (2006.01)
(52) U.S. Cl. .......................... 422/62; 436/56
(58) Field of Classification Search ............ 422/62; 436/55, 56; 252/408.1
  See application file for complete search history.

(56) References Cited

U.S. PATENT DOCUMENTS 5,702,684 A * 12/1997 McCoy et al. ............. 424/10.3
5,900,113 A *  5/1999 Tubergen ..................... 162/49

OTHER PUBLICATIONS

"Corrosive Materials and their Hazards"; Canadian Center for Occupational Health and Safety; published 1997.*

* cited by examiner

*Primary Examiner*—Sean E Conley
(74) *Attorney, Agent, or Firm*—Joshua D. Bishop; Michael B. Martin

(57) ABSTRACT

A method of using an inert fluorescent tracer in a system that contains liquids in contact with solid surfaces and wherein said system contains a corrosive environment, is described and claimed, as is a method of using an inert fluorescent tracer to trace the corrosive material itself. Combinations of inert fluorescent tracers in corrosive materials are also described and claimed.

7 Claims, 2 Drawing Sheets

| Substance Type | Substance Tested | Hydrochloric Acid (37%) | Sulfuric Acid (98%) | Acetic Acid (100%) | Phosphoric Acid (85%) | Sodium Hydroxide (50%) | Dimethyl-formamide (DMF) | Sodium Bicarbonate (ref.) |
|---|---|---|---|---|---|---|---|---|
| Metals | Aluminum | D | D | B | C | D | A | D |
|  | Brass | - | - | D | D | D | - | D |
|  | Bronze | D | B | C | B | C | - | A |
|  | Carpenter 20 | D | A | A | D | B | - | A |
|  | Copper | D | D | B | D | B | A | B |
|  | Hastelloy-C | B | B | A | A | C | - | B |
|  | Titanium | D | D | A | C | B | - | A |
|  | Cast Iron | D | D | D | D | D | - | C |
|  | 304 Stainless Steel | D | C | D | D | B | A | A |
|  | 316 Stainless Steel | D | D | B | D | B | B | A |
| Elastomers | Buna N (Nitrile) | B | C | C | D | A | D | A |
|  | EPDM | C | B | B | B | B | B | A |
|  | Tygon | A | D | D | D | C | D | B |
|  | Viton | A | A | D | A | B | C | A |
|  | Hypalon | B | A | C | B | A | D | A |
|  | PCTFE | A | A | A | A | B | A | A |
|  | Silicone | B | D | B | D | A | C | A |
|  | Natural Rubber | A | D | C | B | A | C | A |
|  | Neoprene | B | D | D | B | B | D | A |
|  | Santoprene | A | D | D | C | A | A | - |
| Non-metals | Carbon Graphite | A | C | A | B | - | - | A |
|  | Ceramic $Al_2O_3$ | C | A | A | A | A | - | A |

FIG. 1A

| Substance Type | Substance Tested | Hydrochloric Acid (37%) | Sulfuric Acid (98%) | Acetic Acid (100%) | Phosphoric Acid (85%) | Sodium Hydroxide (50%) | Dimethyl-formamide (DMF) | Sodium Bicarbonate (ref.) |
|---|---|---|---|---|---|---|---|---|
| Metals | Aluminum | D | D | B | C | D | A | D |
| | Brass | - | - | D | D | D | - | D |
| | Bronze | D | B | C | B | C | - | A |
| | Carpenter 20 | D | A | A | D | B | - | A |
| | Copper | D | D | B | D | B | A | B |
| | Hastelloy-C | B | B | A | A | C | - | B |
| | Titanium | D | D | A | C | B | - | A |
| | Cast Iron | D | D | D | D | D | - | C |
| | 304 Stainless Steel | D | C | D | D | B | A | A |
| | 316 Stainless Steel | D | D | B | D | B | B | A |
| Elastomers | Buna N (Nitrile) | B | C | C | D | A | D | A |
| | EPDM | C | B | B | B | B | B | A |
| | Tygon | A | D | D | D | C | D | B |
| | Viton | A | A | D | A | B | C | A |
| | Hypalon | B | A | C | B | A | D | A |
| | PCTFE | A | A | A | A | B | A | A |
| | Silicone | B | D | B | D | A | C | A |
| | Natural Rubber | A | D | C | B | A | C | A |
| | Neoprene | B | D | D | B | B | D | A |
| | Santoprene | A | D | D | C | A | D | A |
| | | A | C | A | B | - | A | - |
| Non-metals | Carbon Graphite | A | A | A | A | A | - | A |
| | Ceramic Al$_2$O$_3$ | C | A | A | A | A | - | A |

FIG. 1B

| Substance Type | Substance Tested | Hydrochloric Acid (37%) | Sulfuric Acid (98%) | Acetic Acid (100%) | Phosphoric Acid (85%) | Sodium Hydroxide (50%) | Dimethyl-formamide (DMF) | Sodium Bicarbonate (ref.) |
|---|---|---|---|---|---|---|---|---|
| Non-metals | Ceramic Magnet | A | A | A | C | - | - | A |
| Plastics | ABS Plastic | A | - | D | C | A | D | A |
| | Acetal (Delrin) | C | - | D | D | A | D | A |
| | CPVC | A | C | B | A | A | D | A |
| | PVC | B | D | D | B | A | D | A |
| | Epoxy | A | C | B | B | A | D | A |
| | Hytrel | C | C | A | - | C | - | - |
| | NORYL | A | A | A | A | A | D | A |
| | Nylon | D | D | B | B | A | A | A |
| | Polycarbonate | D | D | B | A | D | D | A |
| | PPS (Ryton) | D | A | A | A | A | A | A |
| | HDPE | A | B | A | B | C | A | A |
| | LDPE | B | C | D | B | B | A | A |
| | Polypropylene | C | C | A | A | A | A | A |
| | PTFE (Teflon) | A | A | A | A | A | A | A |
| | PVDF | A | A | A | B | D | D | A |
| | % of substances exhibiting C, D rating -> | 43% | 60% | 39% | 39% | 28% | 54% | 8% |
| | Generally Corrosive >25% of tests receive C, D rating -> | Generally corrosive | Generally corrosive | Generally corrosive | Generally corrosive | Generally corrosive | Generally corrosive | Generally non-corrosive |

*Excerpt of chemical resistance chart information from Cole-Parmer product catalog Y 2003-2004 (p. R-17 to R-26)

METHOD OF TRACING CORROSIVE MATERIALS

CROSS REFERENCE TO RELATED APPLICATION

This application is a continuation-in-part of Ser. No. 10/631,607, filed Jul. 31, 2003 now abandoned, which is herein incorporated by reference.

FIELD OF INVENTION

This invention is in the field of a system that contains a liquid(s) in contact with a solid surface(s), which includes a corrosive environment. Specifically, one embodiment of this invention is in the field of the use of fluorescent tracers in a system where significant amounts of a corrosive material are present.

BACKGROUND OF THE INVENTION

A known difficulty with the use of inert fluorescent tracers in a system that contains a liquid(s) in contact with solid surfaces, e.g. industrial water systems, is the susceptibility of some of them to degradation of their fluorescent signal upon contact, for a sufficient length of time, with corrosive materials. It would be desirable to have inert fluorescent tracers that are capable of maintaining their fluorescent signal in the presence of common corrosive materials.

FIGURE

FIG. 1 shows chemical resistance data for various types of chemistries.

SUMMARY OF THE INVENTION

The first aspect of the instant claimed invention is a method of using one or more inert fluorescent tracers to monitor a system that contains a liquid in contact with a solid surface and wherein said system contains a corrosive environment comprising the steps of: a) adding to the system a treatment chemical wherein said treatment chemical includes one or more inert fluorescent tracers in a known proportion; b) providing one or more fluorometers capable of detecting the fluorescent signal of said inert fluorescent tracers, wherein said fluorometers have a sample cell that corrosive materials can be placed in without rendering the sample cell unusable; c) using said fluorometers to detect and measure the fluorescent signal of said inert fluorescent tracers in the liquid of said system; d) using the detected and measured fluorescent signal to determine how much of the treatment chemical is present in the liquid of said system; and optionally e) adjusting the operating parameters of said system such that the amount of treatment chemical present is optimal for the operating conditions of the system.

The second aspect of the instant claimed invention is a method of tracing a corrosive material, comprising the steps of: a) providing a system that contains a corrosive environment; b) providing a corrosive material that contains one or more inert fluorescent tracers which has a detectable fluorescent signal in said system when placed in said corrosive material, wherein said inert fluorescent tracers are added to said corrosive material in a known proportion; c) adding said corrosive material containing said inert fluorescent tracers to the liquid of said system; d) providing one or more fluorometers capable of detecting the fluorescent signal of said inert fluorescent tracers, wherein said fluorometers have a sample cell that corrosive materials can be placed in without rendering the sample cell unusable; e) using said fluorometers to detect and measure the fluorescent signal of said fluorescent tracers in said system; f) using the detected and measured fluorescent signal to determine how much of the corrosive material is present in the system; and optionally g) adjusting the operating parameters of said system such that the amount of corrosive material present is optimal for the operating conditions of said system.

The third aspect of the instant claimed invention is a composition of matter comprising: a) from about 0.01 ppm to about 10,000 ppm of a compound selected from the group consisting of 1,3,6,8-pyrene tetrasulfonic acid and the known salts of 1,3,6,8-pyrene tetrasulfonic acid; and b) a corrosive material, wherein said corrosive material is selected from the group consisting of concentrated HCl, concentrated $H_2SO_4$, glacial acetic acid, concentrated $H_3PO_4$ and dimethylformamide; wherein concentrated HCl is at least about 37 wt. % HCl in water, concentrated $H_2SO_4$ is at least about 98 wt. % $H_2SO_4$ in water, wherein concentrated $H_3PO_4$ is at least about 85 wt. % $H_3PO_4$ in water; wherein glacial acetic acid is at least about 100 wt. % acetic acid in water and wherein dimethylformamide is about 100 wt. % dimethylformamide.

The fourth aspect of the instant claimed invention is a composition of matter comprising: a) from about 0.01 ppm to about 10,000 ppm of a compound selected from the group consisting of 1,5-naphthalenedisulfonic acid and the known salts of 1,5-naphthalenedisulfonic acid, and b) a corrosive material, wherein said corrosive material is selected from the group consisting of concentrated HCl and concentrated $H_3PO_4$; wherein concentrated HCl is at least about 37 wt. % HCl in water and wherein concentrated $H_3PO_4$ is at least about 85 wt. % $H_3PO_4$ in water.

The fifth aspect of the instant claimed invention is a composition of matter comprising: a) from about 0.01 ppm to about 10,000 ppm of a compound selected from the group consisting of isomers of anthracene disulfonic acid and salts thereof; and b) a corrosive material, wherein said corrosive material is selected from the group consisting of concentrated HCl, concentrated $H_3PO_4$ and dimethylformamide; wherein concentrated HCl is at least about 37 wt. % HCl in water, wherein concentrated $H_3PO_4$ is at least about 85 wt. % $H_3PO_4$ in water and wherein dimethylformamide is about 100 wt. % dimethylformamide.

DETAILED DESCRIPTION OF THE INVENTION

Throughout this patent application the following terms have the indicated definitions.

"CAS#" refers to the Chemical Abstracts Services Registry Number.

"Corrosive environment" refers to an environment where there is at least a "moderate effect" between at least two chemicals when they are in contact with one another. One of ordinary skill in the art would know the meaning of the phrase "moderate effect" in the context of corrosion, e.g. standard chemical resistance charts or compatibility tables delineate the meaning of the phrase "moderate effect". A corrosive environment does not occur when resistance or compatibility tables indicate that there is no effect or a minor effect. A corrosive environment will therefore include a severe effect as defined in compatibility or resistance tables. One reference that discusses compatibility/resistance in the context of corrosion is the Cole Palmer Chemical Resistance Chart (Cole-Palmer Product Catalog Y, 2003-2004, R-17 to R-26). FIG. 1 includes data from Cole Palmer's Chemical Resistance Chart.

The last column of FIG. 1, added by the Applicant's of this invention, highlights one measure of determining when a substance is generally corrosive; a corrosive environment exists when 25% or more of C or D ratings exist for a particular match-up in the table. Tests similar in nature to the standard chemical resistance or chemical compatibility tests or equivalents thereof are included in this definition.

"Corrosive material" refers to a material that acts upon another chemical(s) to produce a corrosive environment in a system that contains the corrosive material and other chemical(s).

Nalco refers to Nalco Company, 1601 W. Diehl Road, Naperville Ill. 60563.

The first aspect of the instant claimed invention is a method of using one or more inert fluorescent tracers to monitor a system that contains a liquid in contact with a solid surface and wherein said system contains a corrosive environment, comprising the steps of: a) adding to the system a treatment chemical wherein said treatment chemical includes one or more inert fluorescent tracers in a known proportion; b) providing one or more fluorometers capable of detecting the fluorescent signal of said inert fluorescent tracers, wherein said fluorometers have a sample cell that corrosive materials can be placed in without rendering the sample cell unusable; c) using said fluorometers to detect and measure the fluorescent signal of said fluorescent tracers in the liquid of said system; d) using the detected and measured fluorescent signal to determine how much of the treatment chemical is present in the liquid of said system; and optionally e) adjusting the operating parameters of said system such that the amount of treatment chemical present is optimal for the operating conditions of the system.

Systems that can contain a corrosive environment include the following: industrial water systems; cooling water systems, including open recirculating, closed and once-through cooling tower water systems; boilers and boiler water systems; petroleum wells, downhole formations, geothermal wells and other oil field applications; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane filtration water systems; food processing streams (meat, vegetable, sugar beets, sugar cane, grain, poultry, fruit and soybean); and waste treatment systems as well as in clarifiers, liquid-solid applications, municipal sewage treatment and industrial or municipal water systems.

Treatment chemicals for use in systems that contain a corrosive environment include commercially available corrosion inhibitors, biological control agents, scale inhibitors, dispersants, coagulants, flocculants, and pH control agents. These commercially available products are well known to people in the art of systems that contain a corrosive environment.

1,3,6,8-pyrene tetrasulfonic acid and the known salts of 1,3,6,8-pyrene tetrasulfonic acid are inert fluorescent tracers that may be used with large amounts of concentrated HCl, concentrated $H_2SO_4$, glacial acetic acid, concentrated $H_3PO_4$ and dimethylformamide; wherein concentrated HCl is at least about 37 wt. % HCl in water, concentrated $H_2SO_4$ is at least about 98 wt. % $H_2SO_4$ in water, wherein concentrated $H_3PO_4$ is at least about 85 wt. % $H_3PO_4$ in water; wherein glacial acetic acid is at least about 100 wt. % acetic acid in water and wherein dimethylformamide is about 100 wt. % dimethylformamide. The preferred known salt of 1,3,6,8-pyrene tetrasulfonic acid for use with corrosive materials is the tetrasodium salt. This material is available from Nalco.

1,5-naphthalenedisulfonic acid and the known salts of 1,5-naphthalenedisulfonic acid disodium salt may be used in water containing large amounts of concentrated HCl and concentrated $H_3PO_4$; wherein concentrated HCl is at least about 37 wt. % HCl in water and wherein concentrated $H_3PO_4$ is at least about 85 wt. % $H_3PO_4$ in water. The preferred known salt of 1,5-naphthalenedisulfonic acid for use with corrosive materials is the disodium salt. This material is available from Nalco.

Isomers of anthracene disulfonic acid and salts thereof may be used in water containing large amounts of concentrated HCl, concentrated $H_3PO_4$ and dimethylformamide; wherein concentrated HCl is at least about 37 wt. % HCl in water, wherein concentrated $H_3PO_4$ is at least about 85 wt. % $H_3PO_4$ in water and wherein dimethylformamide is about 100 wt. % dimethylformamide.

Known isomers of anthracene disulfonic acid, and certain of their known salt forms include the following:

CAS # 13189-75-8 1,5-anthracene disulfonic acid, sodium salt;

CAS # 55750-36-2 1,8-anthracene disulfonic acid sodium salt;

CAS # 61736-91-2 1,5-anthracene disulfonic acid;

CAS # 61736-92-3 1,8-anthracene disulfonic acid;

CAS # 61736-67-2 1,5-anthracene disulfonic acid, magnesium salt;

CAS # 61736-93-4 1,6-anthracene disulfonic acid;

CAS # 61736-94-6 1,7-anthracene disulfonic acid;

CAS# 61736-95-6 2,6-anthracene disulfonic acid; and

CAS# 61736-96-7 2,7-anthracene disulfonic acid.

The preferred isomers of anthracene disulfonic acid are 1,5-antbracene disulfonic acid, magnesium salt, 1,5-anthracene disulfonic acid, sodium salt and 1,8-anthracene disulfonic acid sodium salt and mixtures thereof. The most preferred isomer of anthracene disulfonic acid is about a 2:1 mixture of 1,5-anthracene disulfonic acid, sodium salt and 1,8-anthracene disulfonic acid sodium salt.

Isomers of anthracene disulfonic acid and their known salts can be obtained by following synthetic techniques known in the art of organic chemistry. See GB 1214256, A method of preparing anthraquinone 1,5-disulphonic acid, published Oct. 13, 1976, assigned to Imperial Chemical Industries, Studies on the Sulfonation of Anthracene. Part 1. Sulfonation in neutral or basic solvents, by John O. Morley, Journal of the Chemical Society, Perkin Transactions 2: Physical Organic Chemistry (1972-1999) (1976), (13), 1554-9, Studies on the Sulfonation of Anthracene. Part 2. Sulfonation in acetic acid and related solvents, by John O. Morley, Journal of the Chemical Society, Perkin Transactions 2: Physical Organic Chemistry (1972-1999) (1976), (13), 1560-4.

Fluorometers suitable for use in the instant claimed invention are commercially available from Nalco, these include: TRASAR® 8000, TRASAR® 3000, Xe-2 Fluorometer and a TRASAR® 350. Other suitable fluorometers are available from Spex. The preferred fluorometers are a TRASAR® 3000 unit and a TRASAR® Xe-2 Fluorometer.

How to set up and program a fluorometer and use it to measure the fluorescent signal of a fluorescent tracer is known to people of ordinary skill in the art of fluorometry. After the fluorescent signal of the inert fluorescent tracer is detected and measured, it is known how to correlate that information with the concentration of the inert fluorescent tracer and once the concentration of the inert fluorescent tracer is known that information can be used to determine the amount of treatment chemical present in the system and that information can be used to optimize the operation of the system.

The second aspect of the instant claimed invention is a method of tracing a corrosive material, comprising the steps of: a) providing a system that contains a corrosive environment; b) providing a corrosive material that contains one or more inert fluorescent tracers which has a detectable fluorescent signal in said system when placed in said corrosive material, wherein said inert fluorescent tracers are added to said corrosive material in a known proportion; c) adding said corrosive material containing said inert fluorescent tracers to the liquid of said system; d) providing one or more fluorometers capable of detecting the fluorescent signal of said inert fluorescent tracers, wherein said fluorometers have a sample cell that corrosive materials can be placed in without rendering the sample cell unusable; e) using said fluorometers to detect and measure the fluorescent signal of said fluorescent tracers in said system; f) using the detected and measured fluorescent signal to determine how much of the corrosive material is present in the system; and optionally g) adjusting the operating parameters of said system such that the amount of corrosive material present is optimal for the operating conditions of said system.

The inert tracers that can be used with the specific corrosive materials listed in the first aspect of the instant claimed invention are the same as those that can be used in the second aspect of the instant claimed invention. The fluorometers that can be used in the second aspect of the instant claimed invention are the same as those fluorometers that can be used in the first aspect of the instant claimed invention. How to set up and program a fluorometer and use it to measure the fluorescent signal of a fluorescent tracer is known to people of ordinary skill in the art of fluorometry. After the fluorescent signal of the tracer is detected and measure, it is known how to correlate that information with the concentration of the inert fluorescent tracer and once the concentration of the inert fluorescent tracer is known that information can be used to determine the amount of corrosive material present in the system and that information can be used to optimize the operation of the system.

The third aspect of the instant claimed invention is a composition of matter comprising:
  a) from about 0.01 ppm to about 10,000 ppm of a compound selected from the group consisting of 1,3,6,8-pyrene tetrasulfonic acid and the known salts of 1,3,6,8-pyrene tetrasulfonic acid,
  b) a corrosive material, wherein said corrosive material is selected from the group consisting of concentrated HCl, concentrated $H_2SO_4$, glacial acetic acid, concentrated $H_3PO_4$ and dimethylformamide; wherein concentrated HCl is at least about 37 wt. % HCl in water, concentrated $H_2SO_4$ is at least about 98 wt. % $H_2SO_4$ in water, wherein concentrated $H_3PO_4$ is at least about 85 wt. % $H_3PO_4$ in water; wherein glacial acetic acid is at least about 100 wt. % acetic acid in water and wherein dimethylformamide is about 100 wt. % dimethylformamide.

The amount of 1,3,6,8-pyrene tetrasulfonic acid or a known salt of 1,3,6,8-pyrene tetrasulfonic acid present in the corrosive material is from about 0.01 ppm to about 10,000 ppm, preferably from about 0.05 ppm to about 10 ppm and most preferably from about 0.1 ppm to about 1.0 ppm. The preferred compound is 1,3,6,8-pyrene tetrasulfonic acid, tetrasodium salt.

The fourth aspect of the instant claimed invention is a composition of matter comprising:
  a) from about 0.01 ppm to about 10,000 ppm of a compound selected from the group consisting of 1,5-naphthalenedisulfonic acid and the known salts of 1,5-naphthalenedisulfonic acid, and
  b) a corrosive material, wherein said corrosive material is selected from the group consisting of concentrated HCl and concentrated $H_3PO_4$; wherein concentrated HCl is at least about 37 wt. % HCl in water and wherein concentrated $H_3PO_4$ is at least about 85 wt. % $H_3PO_4$ in water.

The amount of 1,5-naphthalenedisulfonic acid or a known salt of 1,5-naphthalenedisulfonic acid present in the corrosive material is from about 0.01 ppm to about 10,000 ppm, preferably from about 0.05 ppm to about 10 ppm and most preferably from about 0.1 ppm to about 1.0 ppm. The preferred compound is 1,5-naphthalenedisulfonic acid, disodium salt.

The fifth aspect of the instant claimed invention is a composition of matter comprising
  a) from about 0.01 ppm to about 10,000 ppm of a compound selected from the group consisting of isomers of anthracene disulfonic acid and salts thereof, and
  b) a corrosive material, wherein said corrosive material is selected from the group consisting of concentrated HCl, concentrated $H_3PO_4$ and dimethylformamide;
  wherein concentrated HCl is at least about 37 wt. % HCl in water, wherein concentrated $H_3PO_4$ is at least about 85 wt. % $H_3PO_4$ in water and wherein dimethylformamide is about 100 wt. % dimethylformamide.

The amount of isomer of anthracene disulfonic acid and salts thereof present in the corrosive material is from about 0.01 ppm to about 10,000 ppm, preferably from about 0.05 ppm to about 10 ppm and most preferably from about 0.1 ppm to about 1.0 ppm. The preferred isomers of anthracene disulfonic acid are 1,5-anthracene disulfonic acid, magnesium salt, 1,5-anthracene disulfonic acid, sodium salt and 1,8-anthracene disulfonic acid sodium salt and mixtures thereof. The most preferred isomer of anthracene disulfonic acid is about a 2:1 mixture of 1,5-anthracene disulfonic acid, sodium salt and 1,8-anthracene disulfonic acid sodium salt.

The ability to trace a corrosive material is useful for the operation of many different industrial water systems.

The following examples are presented to be illustrative of the present invention and to teach one of ordinary skill how to make and use the invention. These examples are not intended to limit the invention or its protection in any way.

EXAMPLES

Sample Preparation:

Fluorescent tracer solutions (see Table 1) were prepared by adding a specified weighed amount of a stock solution of fluorescent tracer into a corrosion-resistant 250 mL polypropylene bottle. Corrosive liquid solution was added to the propylene bottle containing tracer solution to provide a total volume of 100 mL. The fluorescent tracer and corrosive liquid were mixed. The samples were stored at ambient temperature (approximately 20° C.) for a total of 59 days. Test samples were taken at defined intervals from each traced corrosive liquid solution (initial, 4 days and 59 days) and fluorescence level was measured.

TABLE 1

| Fluorescent Tracer | Stock Solution Concentration* | Amount Added | Test Solution Concentration |
|---|---|---|---|
| Compound 1: 1,5-naphthalenedisulfonic acid, disodium salt | 130 ppm | 0.31 gram | 0.4 ppm |
| Compound 2: 1,3,6,8-pyrenetetrasulfonic acid, tetrasodium salt | 10 ppm | 1.00 gram | 0.1 ppm |
| Compound 3: Fluorescein, monopotassium salt | 0.3 ppm | 3.33 gram | 0.010 ppm |
| Compound 4: 1,5-anthracenedisulfonic acid, magnesium salt | 109 ppm | 0.74 gram | 0.8 ppm |

*Tracer concentration expressed as acid equivalent form

Fluorometer Selection and Set-Up for Detection of Fluorescent Signal

A SPEX fluorometer (Model FluoroMax-2) was used to measure the fluorescent signal and determine dosages of fluorescent tracers being tested in corrosive liquids. The fluorescent signal of each tracer was measured at the excitation and emission wavelengths listed in Table 2. A rectangular quartz cuvette (10 mm×3 mm, inner dimensions) was used to hold the sample. Each combination of fluorescent tracer and corrosive liquid was normalized to 100% in the "initial sample" (Table 3) which was measured within one hour after the tracer and corrosive liquid were mixed. In a few cases (Samples # 6, 16-19, and 21), the fluorescent tracer was not chemically stable with the corrosive liquid being tested and the fluorescent signal quickly decreased to virtually zero. In those cases, the "Initial Sample" was listed as having 0-1% fluorescence and that combination of tracer and corrosive fluid was judged as not acceptable. The fluorescence of the tracer and corrosive liquid solutions were tested again at 4 days and 59 elapsed time. The relative fluorescence of the samples measured at 4 days and 59 days are listed in Table 3. The fluorescence of tracers which change by less than or equal to +/−10% (% relative fluorescence range=90 to 110%, as compared to initial sample) on Day 59 are given an acceptable rating and are defined as being inert over long time periods in the corrosive liquid environment being tested. % relative fluorescence readings on Days 4 and 59 which are greater than 100% indicate an increase in % relative fluorescence, as compared to initial sample. % relative fluorescence readings on Days 4 and 59 which are less than 100% indicate a decrease in % relative fluorescence, as compared to initial sample.

TABLE 2

| Fluorescent Tracer | Excitation Wavelength (nm) | Emission Wavelength (nm) |
|---|---|---|
| 1,5-naphthalenedisulfonic acid, disodium salt | 290 nm | 330 nm |
| 1,3,6,8-pyrenetetrasulfonic acid, tetrasodium salt | 365 nm | 400 nm |
| fluorescein, monopotassium salt | 486 nm | 515 nm |
| 1,5-anthracenedisulfonic acid, magnesium salt | 365 nm | 415 nm |

TABLE 3

Relative Fluorescence over Time of Fluorescent Tracer in Corrosive Liquid Solution

| | | % Relative Fluorescence | | | |
|---|---|---|---|---|---|
| Sample # | Fluid Tested | Initial | 4 days | 59 days | Acceptable* |
| Compound #1 | | | | | |
| 1 | Water^ | 100 | 100 | 100 | yes |
| 2 | Concentrated Hydrochloric Acid (~37% aq. HCl) | 100 | 97 | 95 | yes |
| 3 | Concentrated Sulfuric Acid (98% acid) | 100 | 74 | 0 | no |
| 4 | Glacial Acetic Acid (~100% acid) | >>100** | N/A | N/A | no |
| 5 | Concentrated Phosphoric Acid (~85% H3PO4) | 100 | 98 | 95 | yes |
| 6 | Concentrated Sodium Hydroxide (50% NaOH)^ | 1 | 0 | 0 | no |
| 7 | DMF (100% Dimethylformamide) | 100 | 106 | 115 | no |
| Compound #2 | | | | | |
| 8 | Water^ | 100 | 100 | 100 | yes |
| 9 | Concentrated Hydrochloric Acid (~37% aq. HCl) | 100 | 96 | 94 | yes |
| 10 | Concentrated Sulfuric Acid (98% acid) | 100 | 102 | 102 | yes |
| 11 | Glacial Acetic Acid (~100% acid) | 100 | 102 | 102 | yes |
| 12 | Concentrated Phosphoric Acid (~85% H3PO4) | 100 | 101 | 101 | yes |
| 13 | Concentrated Sodium Hydroxide (50% NaOH)^ | 100 | 2 | 12 | no |
| 14 | DMF (100% Dimethylformamide) | 100 | 99 | 96 | yes |
| Compound #3 These samples are kept in the dark to avoid light degradation of the fluorescein molecule | | | | | |
| 15 | Water^ | 100 | 100 | 100 | yes |
| 16 | Concentrated Hydrochloric Acid (~37% aq. HCl) | 0 | 0 | 0 | no |
| 17 | Concentrated Sulfuric Acid (98% acid) | 0 | 0 | 0 | no |
| 18 | Glacial Acetic Acid (~100% acid) | 0 | 0 | 0 | no |
| 19 | Concentrated Phosphoric Acid (~85% H3PO4) | 0 | 0 | 0 | no |
| 20 | Concentrated Sodium Hydroxide (50% NaOH)^ | 100 | 13 | 2 | no |
| 21 | DMF (100% Dimethylformamide) | 0 | 0 | 0 | no |

TABLE 3-continued

Relative Fluorescence over Time of Fluorescent Tracer in Corrosive Liquid Solution

| | | % Relative Fluorescence | | | |
|---|---|---|---|---|---|
| Sample # | Fluid Tested | Initial | 4 days | 59 days | Acceptable* |
| 1,5-anthracenedisulfonic acid, magnesium salt | | | | | |
| 22 | Water^ | 100 | 100 | 100 | yes |
| 23 | Concentrated Hydrochloric Acid (~37% aq. HCl) | 100 | 97 | 92 | yes |
| 24 | Concentrated Sulfuric Acid (98% acid) | 100 | 53 | 15 | no |
| 25 | Glacial Acetic Acid (~100% acid) | 100 | 70 | 3 | no |
| 26 | Concentrated Phosphoric Acid (~85% H3PO4) | 100 | 100 | 95 | yes |
| 27 | Concentrated Sodium Hydroxide (50% NaOH)^ | 100 | 2 | 0 | no |
| 28 | DMF (100% Dimethylformamide) | 100 | 98 | 95 | yes |

*Acceptable value range is 90-110, which is +/−10% of the initial reference point (100%)
**Not acceptable due to very high background fluorescence
^Comparative Example, not an Example of the invention

TABLE 4

Compilation of Final Results for Fluorescent Tracers in Corrosive Liquid Solutions

| | Fluorescence Results from Day 59 Sample | | | |
|---|---|---|---|---|
| Fluid Tested (listed below) | CMPD #1 | CMPD #2 | CMPD #3 | CMPD #4 |
| Water^ | yes | yes | yes | yes |
| Concentrated HCl (~37% aq. HCl) | yes | yes | no | yes |
| Concentrated H2SO4 (98% acid) | no | yes | no | no |
| Glacial Acetic Acid (~100% acid) | no | yes | no | no |
| Concentrated Phosphoric Acid (~85% H3PO4) | yes | yes | no | yes |
| Concentrated sodium hydroxide (50% NaOH)^ | no | no | no | no |
| DMF (100% dimethylformamide) | no | yes | no | yes |

^Comparative Example, not an Example of the invention
No = not inert (results change by more than +/−10% between initial and Day 59 results), where the word "no" is used, the combination of fluorescent tracer and fluid tested is not an example of the instant claimed invention.
Yes = inert (results change by less than +/−10% between initial and Day 59 results)
CMPD #1 = COMPOUND #1 = 1,5-naphthalenedisulfonic acid, disodium salt
CMPD #2 = COMPOUND #2 = 1,3,6,8-pyrenetetrasulfonic acid, tetrasodium salt
CMPD #3 = COMPOUND #3 = fluorescein, monopotassium salt
CMPD #4 = COMPOUND #4 = 1,5-anthracenedisulfonic acid, magnesium salt

| | Results: Compound | | | |
|---|---|---|---|---|
| Fluid Tested | #1 | #2 | #3 | #4 |
| Water^ | yes | yes | yes | yes |
| Concentrated HCl (~37% aq. HCl) | yes | yes | no | yes |
| Concentrated H2SO4 (98% acid) | no | yes | no | no |
| Glacial Acetic Acid (~100% acid) | no | yes | no | no |
| Concentrated Phosphoric Acid (~85% $H_3PO_4$) | yes | yes | no | yes |
| Concentrated sodium hydroxide (50% NaOH)^ | no | no | no | no |
| DMF (100% dimethylformamide) | no | yes | no | yes |

No = not inert (results change by more than +/−10% between initial and Day 59 results)
Yes = inert (results change by less than +/−10% between initial and Day 59 results)
^comparative example, not an example of the invention
1 = 1,5-naphthalenedisulfonic acid, disodium salt available from Nalco
2 = 1,3,6,8-pyrenetetrasulfonic acid, tetrasodium salt available from Nalco as
3 = fluorescein, monopotassium salt available from Nalco
4 = 1,5-anthracenedisulfonic acid, magnesium salt, available from Nalco The present method has been described in an illustrative manner. Many modifications and variations are possible in light of the above teachings. It is, therefore, to be understood that within the scope of the appended claims the invention may be practiced otherwise than as specifically described.

What is claimed is:

1. A method of tracing a corrosive material, comprising the steps of:
   a) providing a system that contains a liquid;
   b) providing a corrosive material that contains one or more inert fluorescent tracers which has a detectable fluorescent signal in said system when placed in said corrosive material, wherein said inert fluorescent tracers are added to said corrosive material in a known proportion, and wherein said corrosive material is selected from the group consisting of concentrated HCl, concentrated $H_2SO_4$, glacial acetic acid, concentrated $H_3PO_4$ and dimethylformamide;
   c) adding said corrosive material containing said inert fluorescent tracers to a liquid of said system;
   d) providing one or more fluorometers capable of detecting the fluorescent signal of said inert fluorescent tracers, wherein said fluorometers have a sample cell that corrosive materials can be placed in without rendering the sample cell unusable;

e) using said fluorometers to detect and measure the fluorescent signal of said fluorescent tracers in said system;

f) using the detected and measured fluorescent signal to determine how much of the corrosive material is present in the system; and optionally g) adjusting the operating parameters of said system such that the amount of corrosive material present is optimal for the operating conditions of said system.

2. The method of claim 1, wherein said concentrated HCl is at least about 37 wt. % HCl in water, said concentrated $H_2SO_4$ is at least about 98 wt. % $H_2SO_4$ in water, wherein said concentrated $H_3PO_4$ is at least about 85 wt. % $H_3PO_4$ in water, wherein said glacial acetic acid is at least about 100 wt. % acetic acid in water and wherein said dimethylformamide is about 100 wt. % dimethylformamide.

3. The method of claim 1, wherein when said corrosive material is concentrated HCl, said inert tracers are selected from the group consisting of
   a) 1,5-napthalenedisulfonic acid and the known salts of 1,5-napthalenedisulfonic acid,
   b) 1,3,6,8-pyrenetetrasulfonic acid, and the known salts of 1,3,6,8-pyrenetetrasulfonic acid, and
   c) isomers of anthracene disulfonic acid and salts thereof.

4. The method of claim 1, wherein when said corrosive material is concentrated $H_2SO_4$, said inert tracer is 1,3,6,8-pyrenetetrasulfonic acid, tetrasodium salt.

5. The method of claim 1, wherein when said corrosive material is glacial acetic acid, said inert traversed is 1,3,6,8-pyrenetetrasulfonic acid, tetrasodium salt.

6. The method of claim 1, wherein when said corrosive material is concentrated $H_3PO_4$, said inert tracer is selected from the group consisting of
   a) 1,5-napthalenedisulfonic acid and the known salts of 1,5-napthalenedisulfonic acid,
   b) 1,3,6,8-pyrenetetrasulfonic acid, and the known salts of 1,3,6,8-pyrenetetrasulfonic acid, and
   c) isomers of anthracene disulfonic acid and salts thereof.

7. The method of claim 1, wherein when said corrosive material is dimethylformamide, said inert tracers are selected from the group consisting of 1,3,6,8-pyrenetetrasulfonic acid, the known salts of 1,3,6,8-pyrenetetrasulfonic acid, and isomers of anthracene disulfonic acid and salts thereof.

* * * * *